(12) United States Patent
Keane et al.

(10) Patent No.: US 6,951,565 B2
(45) Date of Patent: Oct. 4, 2005

(54) DEVICE FOR INSERTING SURGICAL IMPLANTS

(75) Inventors: Michael Keane, Blue Bell, PA (US); Bill Reimels, Blue Bell, PA (US); Michael Waters, Newtown, PA (US)

(73) Assignee: Linvatec Biomaterials Ltd., Tampere (FI)

( * ) Notice: Subject to any disclaimer, the term of this patent is extended or adjusted under 35 U.S.C. 154(b) by 334 days.

(21) Appl. No.: 10/128,451

(22) Filed: Apr. 24, 2002

(65) Prior Publication Data

US 2003/0204195 A1 Oct. 30, 2003

(51) Int. Cl.[7] .............................................. A61B 17/04
(52) U.S. Cl. ..................... 606/146; 606/104; 606/144; 606/232
(58) Field of Search ............................... 606/146, 232, 606/104, 144

(56) References Cited

U.S. PATENT DOCUMENTS

| 4,968,317 | A | | 11/1990 | Tormala et al. |
| 5,268,001 | A | * | 12/1993 | Nicholson et al. ............ 606/72 |
| 5,578,057 | A | | 11/1996 | Wenstrom, Jr. ............. 606/232 |
| 5,944,739 | A | * | 8/1999 | Zlock et al. ................. 606/232 |

FOREIGN PATENT DOCUMENTS

| EP | 0 577 993 A1 | 1/1994 |
| FR | 2 320 253 | 4/1977 |
| WO | WO 99/21487 | 5/1999 |
| WO | WO 99/35974 | 7/2000 |

* cited by examiner

*Primary Examiner*—Gary Jackson
(74) *Attorney, Agent, or Firm*—Kenyon & Kenyon (57) ABSTRACT

Devices for dispensing suture threads and/or suture threads with needles attached to them that are particularly useful for inserting surgical implants, such as suture anchors, that make use of sutures. The devices use a novel spool design to safely and neatly hold the suture thread and/or needles until the surgeon wishes to dispense them.

55 Claims, 9 Drawing Sheets

DEVICE FOR INSERTING SURGICAL IMPLANTS

FIELD OF THE INVENTION

The device of the present invention is useful for holding and dispensing suture thread and suture thread with needles. It is particularly useful incorporated into a novel device and method for implanting suture anchors or other surgical implants in body tissue. More specifically, the present invention relates to devices that include a spool on which sutures and/or suture needles are wound.

BACKGROUND OF THE INVENTION

Often, doctors have to attach various soft tissues, such as tendons and ligaments, to hard tissue, such as bone. To provide an alternative to suturing the tissue directly through tunnels in the bone, suture anchors have been developed to aid in the attachment of soft tissue to bone. Generally, the doctor will attach such soft tissue to bone by suturing the soft tissue to a suture anchor that has been placed in the bone. During this suturing procedure, the surgeon must pass a suture through the tissue to be repaired, attach it to the suture anchor, and knot the suture so that the tissue is securely fastened to the suture anchor. Often, the suture anchor is prepackaged with sutures and possibly pre-attached needles, thereby obviating the need for the surgeon to pass sutures through the suture anchor himself.

The suture anchor and corresponding sutures are delivered by any number of devices currently commercially available from manufacturers such as Mitek and Arthrex. Typically, the delivery device includes a handle, shaft, suture anchor, and sutures, possibly with needles. The handle is attached to the proximal end of the shaft and the suture anchor is attached to the distal end of the shaft.

The sutures are often attached in some way to the handle or enclosed within it. When the sutures and/or needles are not contained within the handle of the insertion device (for instance, when they are held in a separate tray) the surgeon often has to use two hands to remove the suture and needles from the tray. This can be difficult to accomplish while also holding the insertion instrument. Alternatively, each end of a given suture may have a needle attached thereto, all of which are attached or enclosed within the handle. The suture lengths run along the shaft from the proximal end to the distal end and are threaded through the suture anchor attached to the distal end of the shaft. Often, in these prior art devices, the preattached sutures are easily tangled with each other, adding difficulty and time to the operation, or cannot be dispensed from the handle with only one hand. Further, in the situations in which both sutures and needles are contained in the handle of the device, the needles get entangled with the sutures, or alternatively, must be removed from the handle and/or passed through the shaft of the device, which can be difficult, time consuming, or require two hands to accomplish.

Thus, there is a need in the prior art for a device for inserting suture anchors and/or other suture-containing implants into the body that provides a simple way to insert the implant without tangling the sutures and/or needles.

SUMMARY OF THE INVENTION

The devices of the present invention are useful for holding and dispensing suture thread and suture thread with attached needles. They contain a handle or base with a spool rotatably attached to it, around which the suture thread and needle is wound. In preferred embodiments, the suture thread is dispensed from grooves encircling the spool. Further, in certain preferred embodiments, the handle is capable of contacting or engaging the spool such that at times, the spool cannot rotate so as to unwind the suture. Thus, the suture thread does not unintentionally unwind from the spool. In certain preferred embodiments, the spool contains separate slots for needles that are attached to the suture thread. In still other preferred embodiments of the present invention, the spool contains indentations that are designed to hold and secure the suture thread on the spool so that it does not become tangled or unintentionally unwind from the spool. However, these indentations allow the suture to be released from the suture when desired.

Embodiments of the present invention are particularly advantageous as devices for inserting suture anchors or other surgical implants that make use of suture thread. The devices comprise a handle attached to a longitudinal shaft. The distal end of the shaft holds the surgical implant. Attached to the handle is a spool around which the ends of at least one suture thread is wound, preferably in separate grooves that encircle the surface of the spool. The thread travels from the spool to the distal end of the shaft, where it is threaded through (attached to) the surgical implant. The spool allows for the convenient dispensing of the suture thread, with the use of only one hand, and a low likelihood of tangles in the thread.

In certain preferred embodiments, the device contains two separate suture threads, each of which is threaded through the surgical implant. The two threads preferably are threaded through different eyelets in the surgical implant, so that the tying of knots in one suture thread does not affect the movement of the other suture thread. Where there are two suture threads, the spool preferably has four separate grooves, one for each of the suture ends. These grooves help to keep the suture ends from tangling during the insertion of the surgical implant.

In another preferred embodiment, needles are pre-attached to the ends of the suture thread. The needles, which are curved and roughly semicircular in shape, also fit around the spool. The suture thread can be wound around the spool over the needles, or, in a preferred embodiment, the needles are held on the spool in separate slots. Preferably, at least a portion of the slots containing the needles is located under the surface of the spool. The sharp tip of the needles can be located in this portion of the slot, which serves both to help prevent unwanted movement of the needles on the spool, and also lessens the likelihood of the surgeon or other hospital personnel being stuck by a needle.

The spool also preferably has indentations which are capable of securing the suture thread, thereby helping to prevent unwanted movement of the needles and the suture thread on the spool. In embodiments where the needles are located in the same grooves as the suture thread, and the suture thread is wound around the spool on top of the needles indentations for holding the suture threads may be located at the bottom of the grooves. In embodiments where the needles are located in separate slots that are adjacent to the grooves where the thread is wound, the indentations for holding the thread are preferably located adjacent to the slots. While these indentations serve to hold the suture thread in place, they also allow the suture thread to be unwound from the spool when desired. In other words, the surgeon can easily remove the sutures from these indentations when desired.

In yet another preferred embodiment of the present invention, the spool will rotate in a direction that will cause the suture thread to unwind only when desired by the surgeon. This can preferably be achieved by a portion of the handle temporarily contacting or engaging the spool, thereby preventing the unwanted rotation or unwinding of the suture thread. When the surgeon wishes to allow the suture thread to unwind from the spool, he releases the contact between the handle and the spool, thereby allowing the spool to rotate freely. This prevents unwanted slack in the suture thread during the insertion of the surgical device, and helps to prevent tangling of the suture thread. The tautness of the suture thread also helps to keep the anchor suture positioned on the distal end of the shaft of the device. It is further preferable that the particular mechanism used to prevent the unwinding of the suture thread can be disengaged with only one hand, allowing the surgeon one free hand.

In certain preferred embodiments, the spool is located inside the handle of the device. In such embodiments, the handle may have a door that, when closed, contacts the spool, preventing its motion in the direction that would cause the suture thread to unwind. This contact is preferably caused by a protuberance on the inside of the door that engages one of a series of notches (indentations) or teeth, on the spool. When the door is opened, preferably by pivoting, rotating, or sliding it open, the spool is no longer engaged by the door and can freely rotate.

The distal end of the shaft preferably contains a recess for holding at least the proximal portion of the surgical implant. In a further preferred embodiment, the distal end of the shaft contains a longitudinal slot extending from the distal tip of the shaft towards the proximal (handle) end of the shaft. The suture threads may be positioned within this slot, thereby helping to keep the threads away from the distal tip of the shaft during the insertion of the surgical implant, and allowing the threads to help keep the implant properly positioned on the distal end of the shaft. Once the implant is inserted into the tissue being repaired, however, the slot allows the thread to pass completely outside of the shaft, allowing the surgeon to easily unwind the thread and any needles from the spool.

While the devices of the present invention may be used to insert any surgical implant that makes use of suture thread, it is most preferably used for inserting suture anchors. These suture anchors are preferably screwed into the tissue to be repaired, by rotating the handle and shaft as one would a screwdriver, or may be pushed into the tissue to be repaired, even by tapping the end of the device with a mallet or hammer, to force the suture anchor into the tissue to be repaired. However, in either case, once the suture anchor is inserted into the tissue to be repaired, it is easily removed from the distal end of the shaft, preferably simply by pulling the shaft away from the inserted implant.

The present invention also includes methods for inserting surgical implants in vivo using the aforementioned devices.

DETAILED DESCRIPTION OF THE INVENTION

The present invention provides an apparatus that, e.g., allows convenient placement of suture anchors or other devices that use suture thread to attach body tissue to body tissue or to bone.

Figure 1:
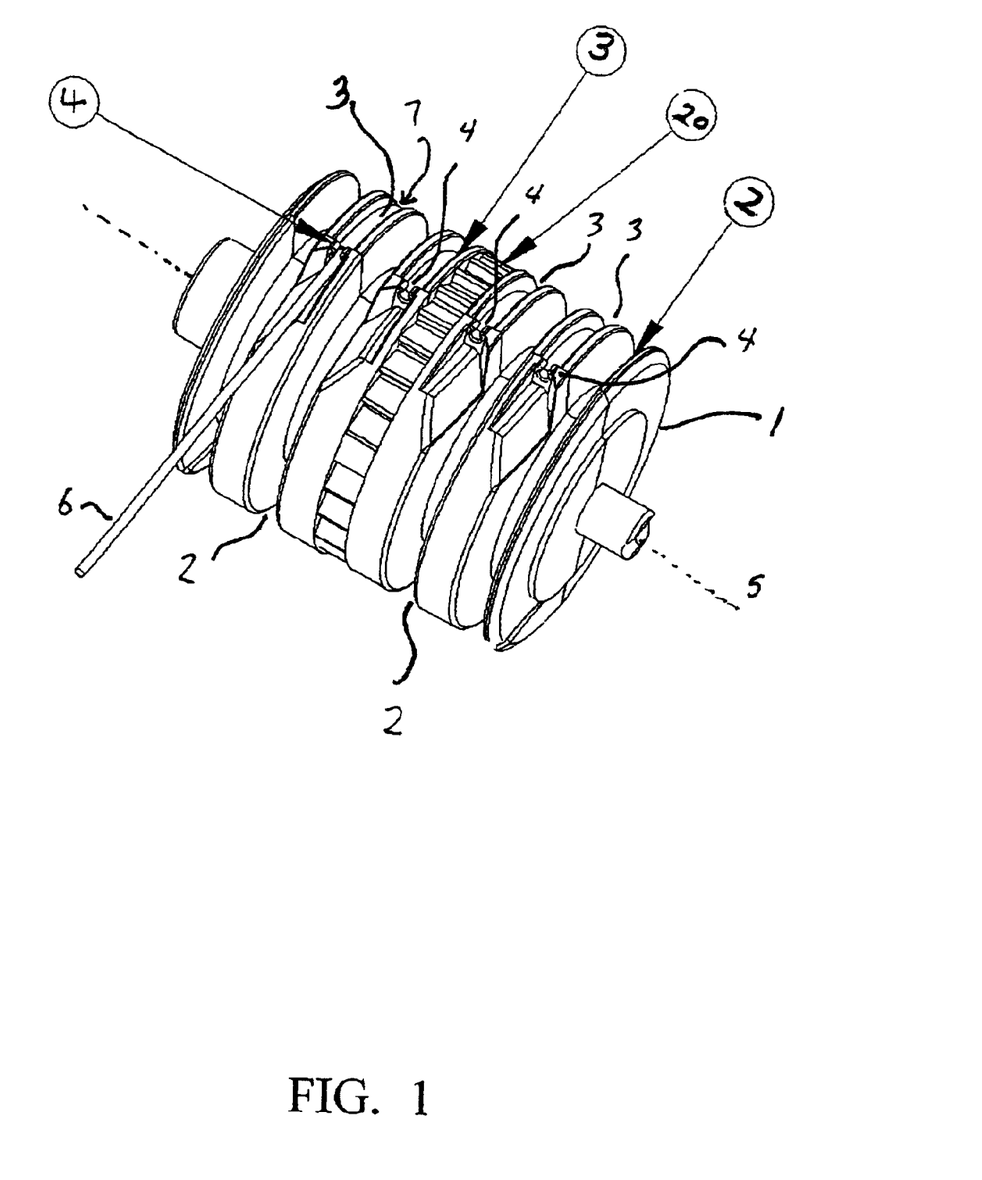
FIG. 1 shows a perspective view of an embodiment of a spool used in the present invention.

The present invention uses a novel spool system that secures sutures and even needles attached to the sutures, and allows for easy delivery of them by a surgeon. The spool allows the suture to be delivered quickly with little risk of tangling, and little risk of accidentally getting stuck with the needles. FIG. 1 shows a preferred embodiment of the spool 1 used in the present invention around which sutures 6 and suture needles 7 may be wound.

In the particular embodiment of FIG. 1, the spool 1 is a cylinder shaped member, which is capable of rotating around a central axis 5. The spool 1 has several grooves 2 encircling its surface, for receiving suture thread. There preferably is a separate groove 2 for each end of the suture thread being dispensed. Thus, for a spool that dispenses two separate suture threads, there are preferably four grooves 2 for receiving the ends of each of the two suture threads. The separate grooves for each end of the suture thread helps to prevent tangling of the suture threads. The grooves 2 are preferably deep enough so that the suture thread may be wound around the spool 1 while remaining inside the groove 2. Again this helps keep the suture thread in the groove 2, which helps to prevent tangling of the suture. While the embodiment of FIG. 1 has four grooves 2 for receiving the ends of two separate suture threads, other embodiments could have a different number of grooves for accommodating one or more suture threads.

In the particular preferred embodiment of FIG. 1, the spool 1 also has slots 3 for holding needles that are attached to the ends of the suture threads. Each slot 3 is preferably adjacent to a groove 2, so that the needle that is attached to a particular suture thread is located on the spool 1 next to the suture thread itself. A portion of the slot 3 preferably tunnels under the surface of the spool 1 (i.e., leads to a recess under the surface of the spool 1), and holds the sharp tip of the needle. This helps to keep the needle from moving from the slot 3, and also helps prevent hospital personnel from accidentally sticking themselves with the suture needles. The slot 3 is preferably as deep as the width of the needle, so that the needle can be stored completely within the slot 3. In FIG. 1, one of the slots 3 has a needle 7 located within it. As can be seen in FIG. 1, the slot is deep enough to hold the needle 7.

The suture needles that are used with the present invention are generally curved into a semicircular shape, and therefore may be placed around the spool. While it is preferred, there need not be separate slots for the needles on the spool. The needles could be located, e.g., at the bottom of the grooves 2, with the suture thread wound around the spool 1 in the groove on top of the needle. This may result in the diameter of the spool being larger, however.

In the preferred embodiment of FIG. 1, there are also indentations 4 for securing the suture thread. In FIG. 1, the indentations are located on the surface of the spool 1, adjacent to the slots 3 which hold the needles that may be attached to the sutures. The suture thread is pushed into the indentation 4, which then helps to hold the suture thread in place. Due to the placement of the indentations 4, this also helps to hold the needles in place. In the embodiment of FIG. 1, the indentations 4 are narrower at the top than at the bottom, and are tear-drop shaped. Preferably the narrow portion of the indentation is slightly smaller than the width of the suture thread, so that the suture thread (being somewhat compressible) can be pushed through the narrow portion of the indentation 4, and will likely remain in the wider portion of the indentation 4 until removed by the surgeon. Thus, the indentation 4 secures the suture thread. Other shapes for the indentation 4 can be used as part of the present invention. Moreover, the sutures can be held in place with structures other than simple indentations, such as a variety of clasps. While not shown in FIG. 1, the spool 1 could also include indentations or other mechanisms for holding the needles themselves in place, instead of or in addition to the indentations or other mechanisms for holding the suture threads in place.

In the situation where suture needles are located in the same grooves as the suture thread, indentations or other mechanisms for securing the suture thread may be located at the bottom of the grooves, adjacent to the needles. This would help to prevent the needle from accidentally falling off the spool when the suture thread is being unwound.

Also shown in FIG. 1 are a series of triangular notches 20 encircling the circumference of the spool. These notches 20 are designed to temporarily contact a movable protuberance on the handle or base to which the spool 1 is attached, thereby preventing the spool 1 from rotating in the direction that would cause the suture thread to unwind from the spool 1. When the contact between the handle or base and the spool is released, the spool can rotate freely. This mechanism helps to prevent unwanted or unintended unwinding of the suture thread. While, in FIG. 1, the notches 20 are located in the center of the spool 1, they could be towards the sides of the spool 1, or even on the sides of the spool 1. Further, there need not be a series of triangular notches. There could be only one notch of a variety of shapes. Further, there could be a protuberance, instead of a notch, that contacts the handle or base to which the spool is attached and prevents the rotation of the spool in the direction that would cause the suture thread to unwind. In other embodiments, there need be no special indentation or protuberance, or series of indentations or protuberances on the spool to prevent the unwanted rotation, so long as some portion of the handle or base makes suitable contact with some portion of the spool.

The spool is preferably made out of molded plastic, but can be made of other materials, or through other well-known manufacturing techniques. A benefit of molded plastic is that it allows the spool to be manufactured inexpensively.

Figure 2:
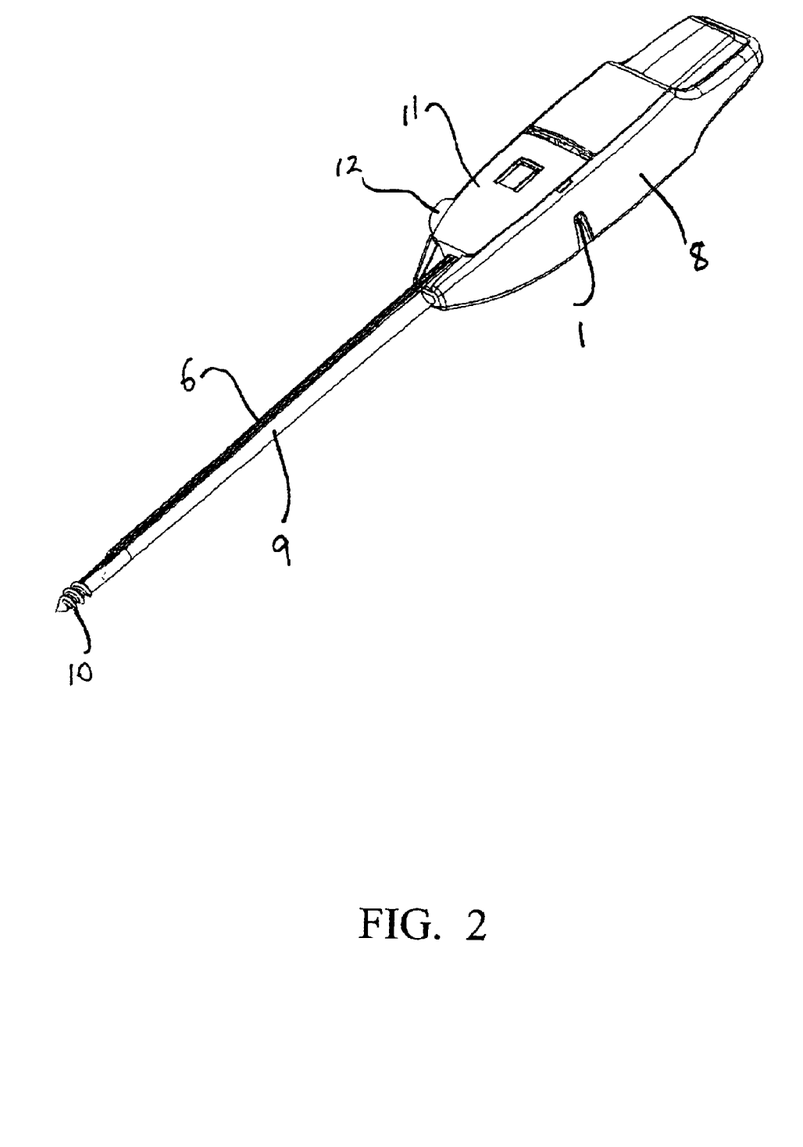
FIG. 2 shows an embodiment of the present invention useful for inserting suture anchors in vivo.

FIG. 2 shows an embodiment of a device of the present invention for inserting suture anchors that uses the spool shown in FIG. 1. The device has a handle 8. Attached to the distal end of the handle is a longitudinal shaft 9. In the embodiment of FIG. 2, the spool 1 is located inside the handle 8. In other embodiments of the present invention, the spool can be attached to the exterior of the handle. Having the spool enclosed within the handle allows the handle to be easily gripped and rotated by the surgeon, and also lessens the likelihood that the sutures wound around the handle will be tangled or disturbed. Further, if the sutures have needles attached to them, the location of the spool inside the handle helps to lessen the likelihood of surgical personnel being unintentionally stuck by the needles.

In the embodiment of FIG. 2, the handle 8 has a door portion 11, which allows access to the spool 1. An extension 12 of the door portion 11 extends beyond the side of the handle 8, allowing the door portion 11 to be opened with the same hand the surgeon is using to hold the handle 8. While the door portion 11 pivots open in the embodiment of FIG. 2, it could be opened in other ways, such as by rotating or by sliding.

The suture threads 6 can be seen exiting the handle 8 and traveling to the distal end of the shaft 9, where the suture anchor 10 is located. The suture threads are threaded through (attached to) the suture anchor 10.

Figure 3:
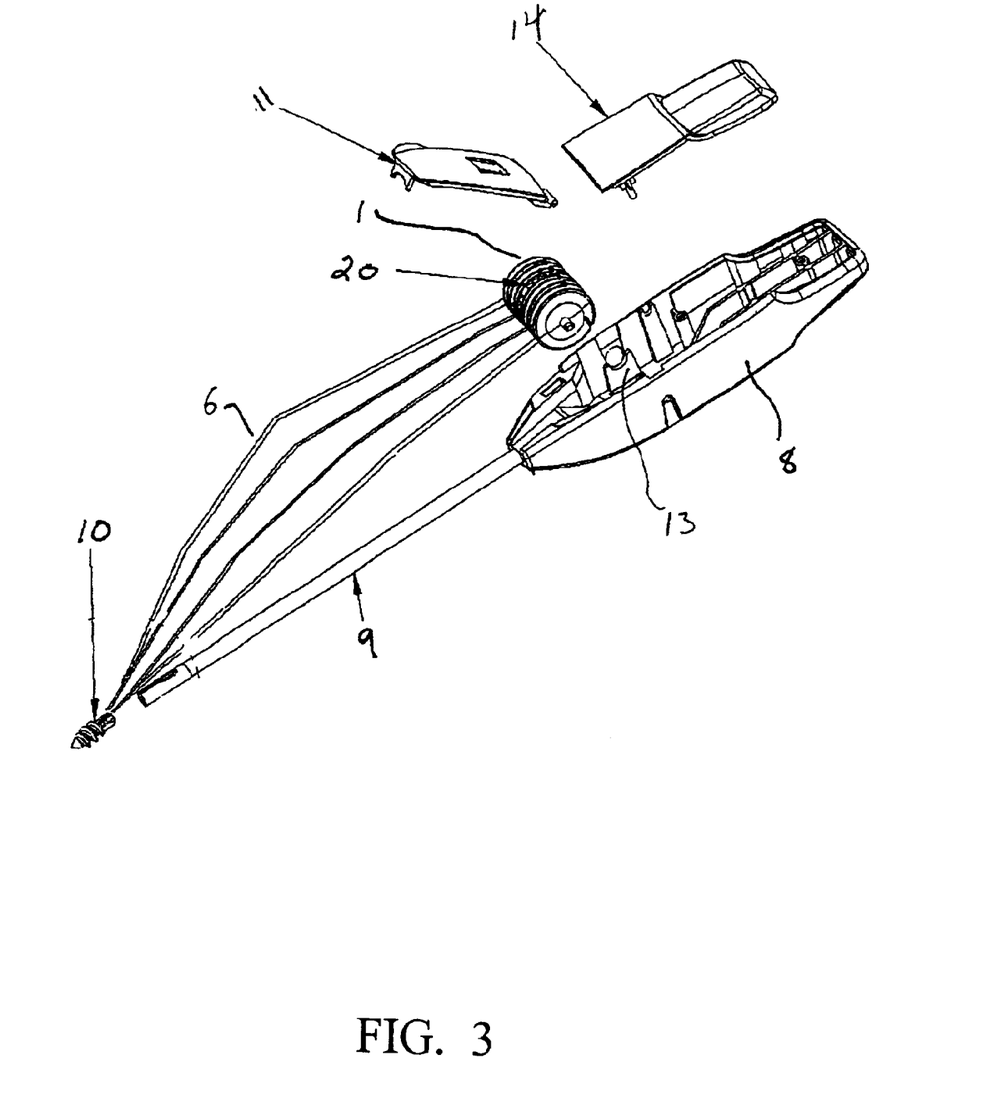
FIG. 3 shows an exploded view of the embodiment of FIG. 2.

FIG. 3 shows an exploded view of the embodiment of FIG. 2. In FIG. 3, the interior chamber 13 of the handle 8, where the spool 1 is placed, can be seen, because the door portion 11 and a handle cover 14 are shown removed from the handle 8. The underside of the door portion 11 contains a protuberance (not seen) that contacts one of the series of triangular notches 20 located on the spool 1 when the door portion 11 is closed. When the door portion 11 is closed (as shown in FIG. 2), the spool 1 is prevented from rotating in the direction that would cause the suture thread to unwind by the contact between the door portion 11 and the spool 1. When the door portion 11 is opened, then it no longer contacts the spool 1, and the spool 1 may rotate freely, allowing the surgeon to unwind the suture thread.

The contact between the door portion 11 and the spool 1 need not be the result of a protuberance on the interior of the door portion 11 contacting one of a series of notches 20 in the center of the spool 1. Any type of temporary contact between the door portion 11 and any part of the spool 1 could act to prevent unwanted rotation of the spool 1. Further, while in FIGS. 2 and 3, the door portion 11 is pivoted open to release the contact between it and the spool 1, the contact could be released in several different ways. For instance, the door portion 11 could slide or rotate, thereby releasing the contact between it and the spool 1. Further, there could be a button, switch, or lever on the handle 8 that the surgeon presses or moves to release the contact with the spool 1 that is preventing unwanted rotation of the spool.

Further, the spool 1 could have temporary contact with a part of the handle 8 other than the door portion 11 to prevent unwanted rotation of the spool 1. This could be the case, for instance, in embodiments where the spool is not located inside of the handle. Such contact could be disengaged, thereby allowing the spool to rotate freely, by pivoting, sliding, rotating, or otherwise moving the portion of the handle that is in contact with the spool, or even by moving the spool itself. Further, the contact with the spool could be released by the surgeon pressing a button or moving a switch or lever which in turn releases the contact between the spool and the handle that prevents the unwanted rotation of the spool. The means for preventing the rotation of the spool thus can include any means for providing temporary contact with the spool, provided that the contact is sufficient to prevent the spool from rotating at least in the direction that would cause the suture thread to unwind.

Figure 4:
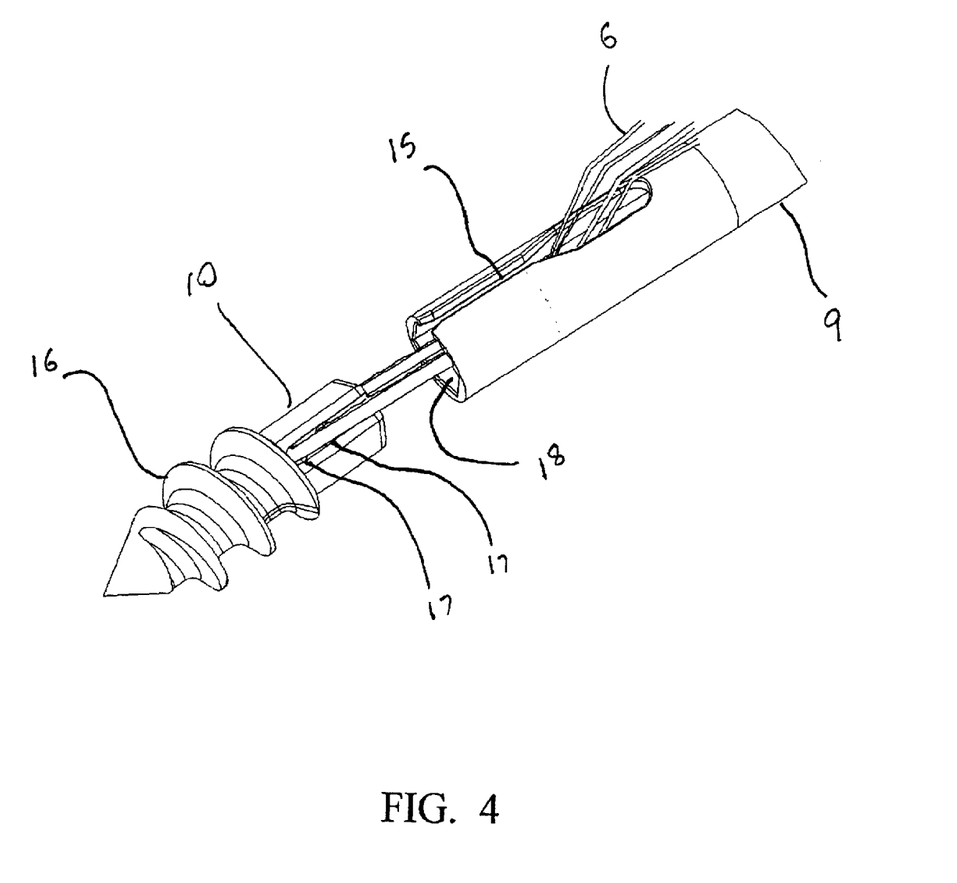
FIG. 4 shows a side view of the distal end of the embodiment of FIG. 2.

FIG. 4 shows a close-up view of the distal portion of the shaft 9 of the device of FIG. 2, with the suture anchor 10 positioned slightly away from the shaft 9. As can be seen, the suture threads 6 are threaded through the suture anchor 10. In a preferred embodiment, each suture thread is threaded through a different hole 17 of the suture anchor 10, so that the threads move more independently of each other when eventually being tied by the surgeon. Thus, in the embodiment of FIG. 4, there are two suture threads and the suture anchor 10 has two holes 17, each for receiving one of the suture threads. Nevertheless, the suture anchor need not have a separate hole for each suture thread, particularly in very small suture anchors.

In the embodiment of FIG. 4, the suture anchor 10 has screw threads 16. This allows the suture anchor 10 to be screwed into the tissue to be repaired by the surgeon. In this embodiment, the handle and shaft of the device are used as a screwdriver to insert the suture anchor. Depending on the area to be treated, the surgeon may screw the suture anchor into a predrilled hole. In other embodiments, the insertion device of the present invention may be used to insert suture anchors or other surgical implants in different ways, such as by pushing them, or even allowing them to be hammered into the tissue to be repaired.

The suture anchors used with the present invention are preferably made of self-reinforced bioabsorbable polymeric material, as described, for instance, in U.S. Pat. No. 4,968,317, which is hereby incorporated fully by reference. One material that is particularly useful for making suture anchors that can be used with the present invention is self-reinforced (96/4D) PLA copolymer.

In the preferred embodiment of FIG. 4, the distal portion of the shaft 9 contains a recess 18, into which the proximal portion of the suture anchor 10 can be securely placed. The suture anchor 10 is held securely in the recess until the suture anchor 10 is inserted in the tissue to be repaired, at which time the suture anchor 10 may be easily removed from the recess 18 in the distal portion of the shaft 9 by simply pulling the shaft 9 away from the suture anchor 10. The closer the interior dimensions of the recess 18 are to the exterior dimensions of the proximal end of the suture anchor 10, the more securely the suture anchor 10 will be held in the recess 18. In certain preferred embodiments, the suture anchor 10 is also held securely on the distal portion of the shaft 9 as a result of the taut suture threads 6, which prevent the suture anchor 10 from moving distally away from the shaft 9 until the surgeon releases the spool.

As shown in FIG. 4, in a preferred embodiment of the present invention, the distal portion of the shaft 9 contains a slot 15. The slot 15 extends from the distal tip of the shaft 9 towards the proximal (handle) end of the shaft. The suture threads 6 travel from the spool—located in, on, or near the handle of the device—outside the shaft to the slot 15, where the suture threads enter the slot 15, and the recess 18, where the suture anchor 10 is located. In the preferred embodiment of FIG. 4, the slot 15 is wider at its proximal end than at its distal end. This helps provide room for the suture threads 6 at the proximal area where they enter the slot 15, yet helps to prevent the threads 6 from exiting the slot 15 completely before the surgeon implants the suture anchor 10 in the tissue to be repaired. Once the suture anchor 10 is inserted in the tissue to be repaired, the slot 15 allows the surgeon to completely remove the suture thread from the shaft 9, simply by pulling the distal portion of the thread through the slot 15, thereby releasing it entirely from the shaft 9. If the slot 15 did not extend all the way to the distal end of the shaft 9, this would not be possible and the suture thread, and any needles attached thereto, would have to be passed in their entirety through the slot 15 in the shaft 9. While in FIG. 4, the suture threads are located outside of the shaft until they enter the slot 15, in other embodiments of the present invention, the suture threads may travel from the spool to the implant through the entire length of the shaft.

Figure 5:
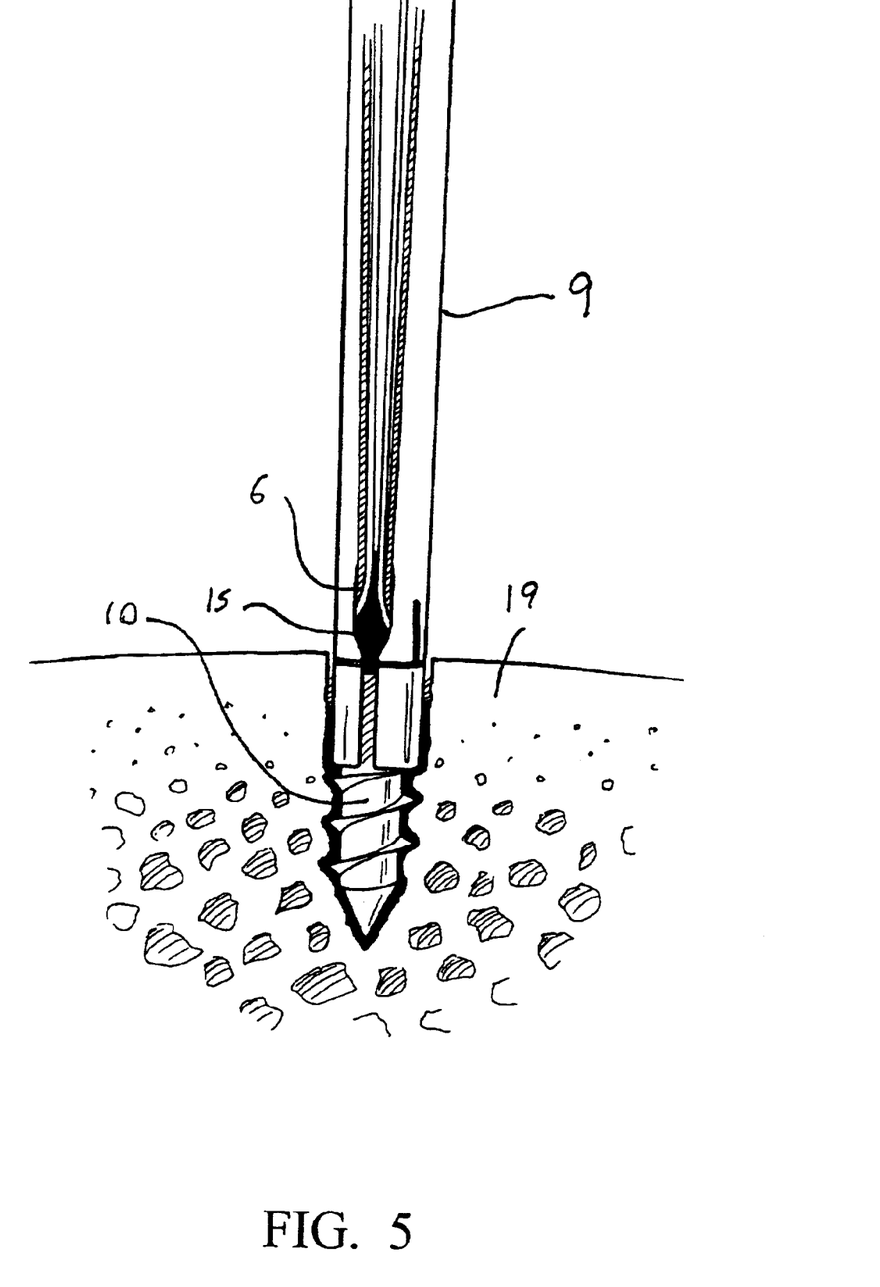
FIGS. 5–9 show side views of an embodiment of the present invention during various stages of its use in a surgical procedure to insert a suture anchor.

FIG. 5 shows the preferred embodiment of FIG. 2 being used to insert a suture anchor 10 into bone 19. The suture anchor 10 has been screwed into the bone 19 through a precut channel. The suture threads 6 are running along the outside of the shaft 9, and pass through the slot 15, where they are threaded through the suture anchor 10. For ease of reference by the surgeon, when two separate suture threads are used with the device of the present invention, it is preferable that they are different colors.

Figure 6:
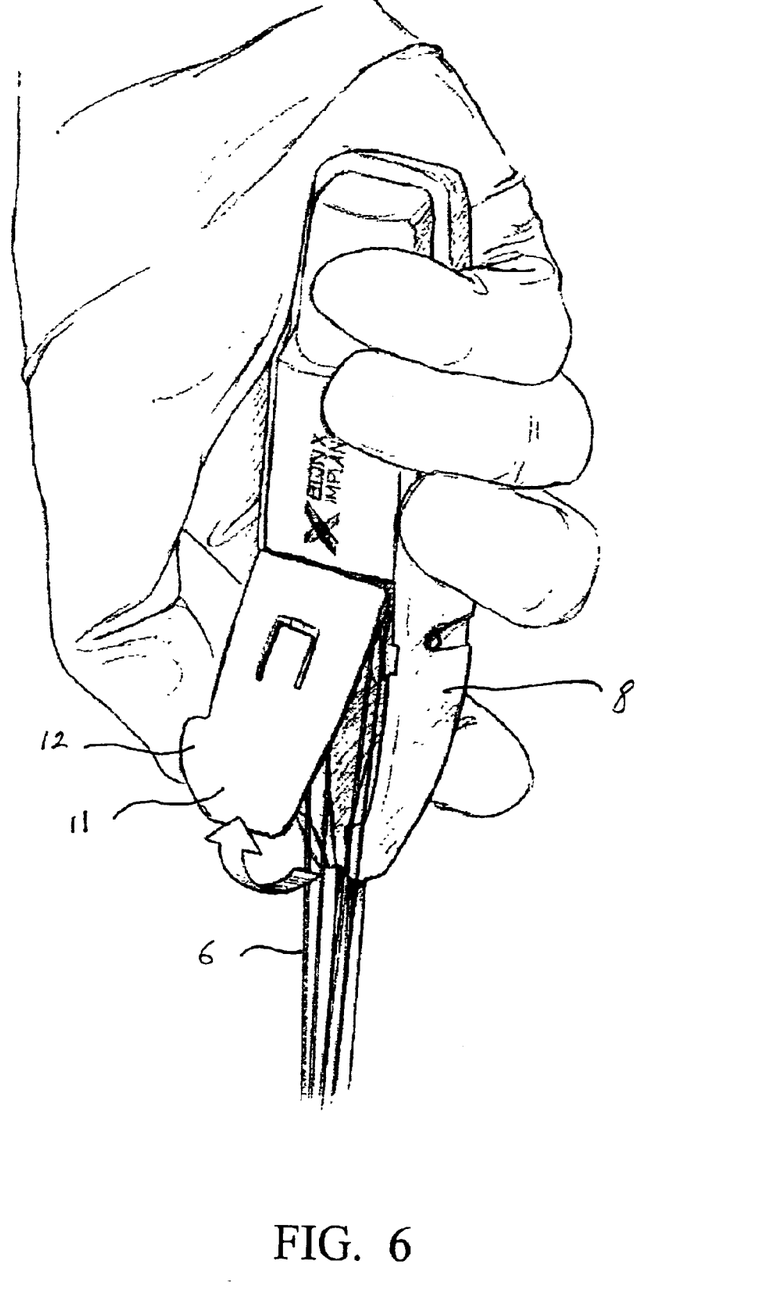

FIG. 6 shows the surgeon opening the door portion 11 of the handle 8 with the hand that is holding the handle 8, by pushing his thumb against the extension 12 of the door portion 11 that extends beyond the side of the handle 8. This causes the door portion 11 to disengage its contact with the spool, thereby allowing the spool to rotate freely and allowing the suture threads 6 to unwind from the spool.

Figure 7:
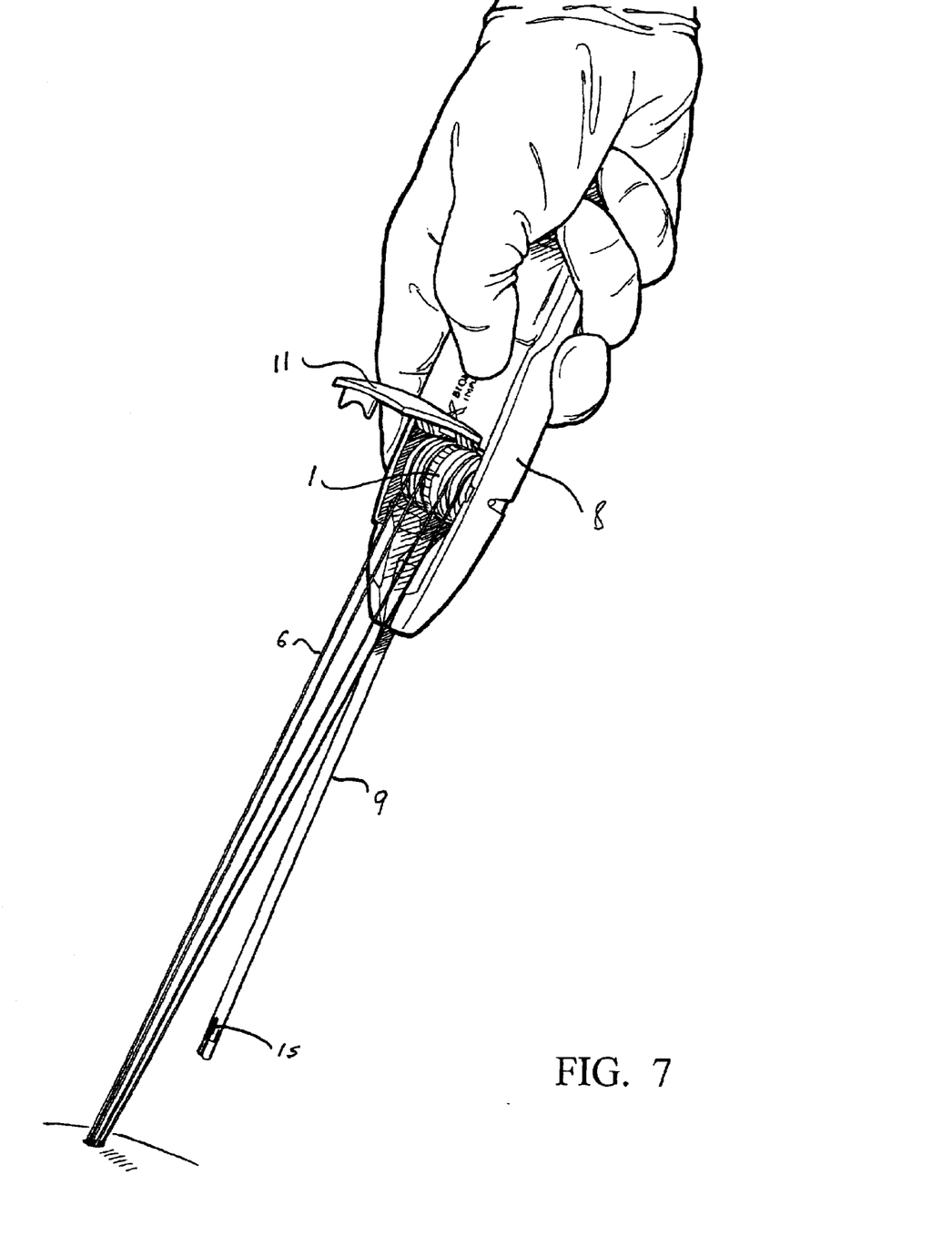

FIG. 7 shows the surgeon pulling the device away from the inserted suture anchor. As the surgeon pulls the device away from the suture anchor, the suture threads 6 have slipped through the slot 15 and are completely external to the shaft 9. The suture threads 6 are unwinding from the spool 1, which is free to rotate now that the door portion 11 is opened. Once the suture thread has completely unwound, the needles will be released from the spool.

Figure 8:
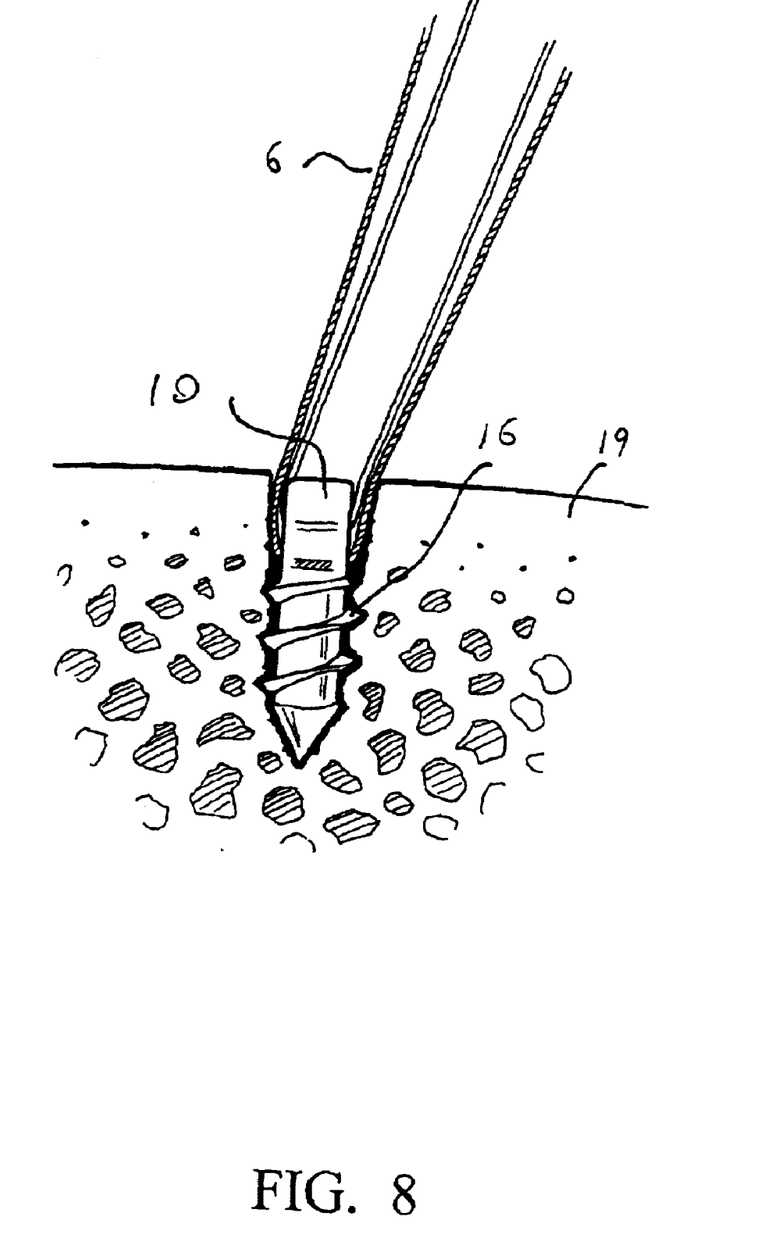

FIG. 8 shows the implanted suture anchor 10. Its screw threads 16 are holding it securely in the bone 19 into which it has been inserted. The suture threads 6 are still attached to the suture anchor 10.

Figure 9:
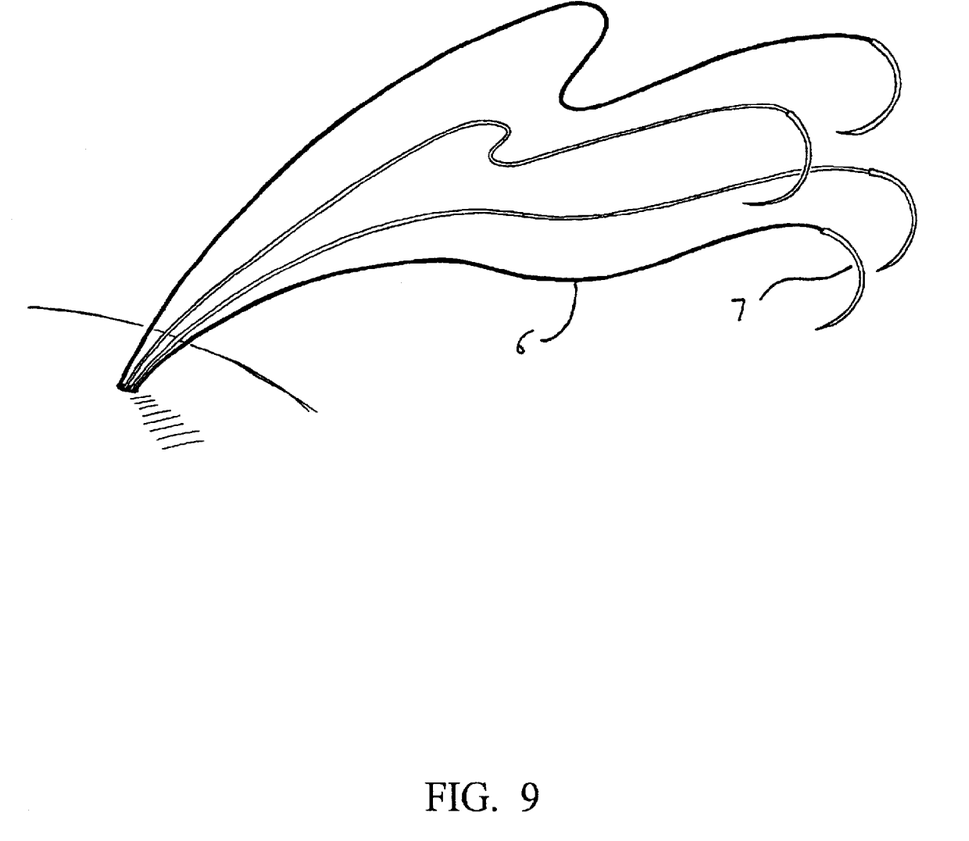

FIG. 9 shows the suture threads 6, with their attached needles 7 after they have been completely unwound and removed from the spool of the device. At this point, the threads, which are not tangled, may be passed through body tissue and knotted so as to effect the surgical repair being performed, e.g., the attachment of tendon to bone. While in the embodiment shown in FIG. 9 the sutures have needles attached to their ends, the suture threads used in conjunction with the present invention need not have needles pre-attached to them.

After the description above of the present invention and certain specific embodiments thereof, it will be readily apparent to those skilled in the art that many variations and modifications may be made to the present invention without departing from the spirit and scope thereof.

We claim:

1. An apparatus for holding and dispensing sutures comprising:
   a handle; and
   a spool rotatably attached to said handle, the spool comprising:
   a first groove encircling the circumference of the spool;
   a second groove encircling the circumference of the spool; and
   at least one notch for temporarily engaging with at least a portion of the handle and preventing the rotation of the spool in at least one direction with respect to the handle.

2. The apparatus of claim 1, wherein the spool further comprises:
   a first slot adjacent to the first groove; and
   a second slot adjacent to the second groove.

3. The apparatus of claim 2, wherein at least a portion of the first slot is located under the surface of the spool, and wherein at least a portion of the second slot is located under the surface of the spool.

4. The apparatus of claim 2, wherein the spool further comprises:
   a first indentation adjacent to the first slot for removably receiving and securing a suture; and
   a second indentation adjacent to the second slot for removably receiving and securing a suture.

5. The apparatus of claim 4, wherein the first and second indentations are narrower at the top than at the bottom.

6. The apparatus of claim 5, wherein the first and second indentations are tear-drop shaped.

7. An apparatus for holding and dispensing sutures or sutures with needles comprising:
a handle; and
a spool rotatably attached to said handle, the spool comprising:
a first groove encircling the circumference of the spool;
a second groove encircling the circumference of the spool; and
at least one protuberance for temporarily engaging with at least a portion of the handle and preventing the rotation of the spool in at least one direction with respect to the handle.

8. The apparatus of claim 7, wherein the spool further comprises:
a first slot adjacent to the first groove; and
a second slot adjacent to the second groove.

9. The apparatus of claim 8, wherein at least a portion of the first slot is located under the surface of the spool, and wherein at least a portion of the second slot is located under the surface of the spool.

10. The apparatus of claim 8, wherein the spool further comprises:
a first indentation adjacent to the first slot for removably receiving and securing a suture; and
a second indentation adjacent to the second slot for removably receiving and securing a suture.

11. The apparatus of claim 10, wherein the first and second indentations are narrower at the top than at the bottom.

12. The apparatus of claim 11, wherein the first and second indentations are tear-drop shaped.

13. An apparatus for holding and dispensing sutures or sutures with needles comprising:
a handle;
a spool rotatably attached to said handle, the spool comprising:
a first groove encircling the circumference of the spool;
a second groove encircling the circumference of the spool; and means for temporarily preventing the rotation of the spool in at least one direction with respect to the handle.

14. The apparatus of claim 13, wherein the spool further comprises:
a first slot adjacent to the first groove; and
a second slot adjacent to the second groove.

15. The apparatus of claim 14, wherein at least a portion of the first slot is located under the surface of the spool, and wherein at least a portion of the second slot is located under the surface of the spool.

16. The apparatus of claim 14, wherein the spool further comprises:
a first indentation adjacent to the first slot for removably receiving and securing a suture; and
a second indentation adjacent to the second slot for removably receiving and securing a suture.

17. The apparatus of claim 16, wherein the first and second indentations are narrower at the top than at the bottom.

18. The apparatus of claim 17, wherein the first and second indentations are tear-drop shaped.

19. The apparatus of claim 16, further comprising a suture having first and second ends, wherein the first end is wound around the spool in the first groove and the second end is wound around the spool in the second groove.

20. The apparatus of claim 19, wherein the first end of the suture has a first needle attached thereto and the second end of the suture has a second needle attached thereto; and further wherein, the first needle is located in the first slot, and the second needle is located in the second slot.

21. The apparatus of claim 20 wherein a portion of the suture adjacent to the first needle is located in the first indentation, and wherein a portion of the suture adjacent to the second needle is located in the second indentation.

22. The apparatus of claim 14, wherein the spool further comprises:
a third groove encircling the circumference of the spool;
a fourth groove encircling the circumference of the spool;
a third slot adjacent to the third groove; and
a fourth slot adjacent to the fourth groove.

23. The apparatus of claim 22, wherein the spool further comprises:
a first indentation adjacent to the first slot for removably receiving and securing a suture;
a second indentation adjacent to the second slot for removably receiving and securing a suture;
a third indentation adjacent to the third slot for removably receiving and securing a suture;
a fourth indentation adjacent to the fourth slot for removably receiving and securing a suture.

24. The apparatus of claim 23, wherein the first, second, third, and fourth indentations are tear-drop shaped.

25. The apparatus of claim 23, further comprising:
a first suture having first and second ends, wherein the first end of the first suture is wound around the spool in the first groove and the second end of the first suture is wound around the spool in the second groove; and
a second suture having first and second ends, wherein the first end of the second suture is wound around the spool in the third groove and the second end of the second suture is wound around the spool in the fourth groove.

26. The apparatus of claim 25, wherein the first end of the first suture has a first needle attached thereto, the second end of the first suture has a second needle attached thereto, the first end of the second suture has a third needle attached thereto and the second end of the second suture has a fourth needle attached thereto; and
further wherein, the first needle is located in the first slot, the second needle is located in the second slot, the third needle is located in the third slot, and the fourth needle is located in the fourth slot.

27. The apparatus of claim 26 wherein a portion of the first suture adjacent to the first needle is located in the first indentation, wherein a portion of the first suture adjacent to the second needle is located in the second indentation, wherein a portion of the second suture adjacent to the third needle is located in the third indentation, and wherein a portion of the second suture adjacent to the fourth needle is located in the fourth indentation.

28. The apparatus of claim 13; wherein the spool further comprises:
a third groove encircling the circumference of the spool; and
a fourth groove encircling the circumference of the spool.

29. The apparatus of claim 13 wherein the means for temporarily preventing the rotation of the spool comprises a portion of the handle that removably contacts the spool.

30. An apparatus for inserting surgical implants in vivo, comprising:
a handle;
a spool rotatably attached to the handle, the spool comprising at least two grooves;

at least one suture having a first end and a second end, wherein each end of the at least one suture is wound around the spool and located in a separate one of the at least two grooves;

a shaft having distal and proximal ends, wherein the proximal end is attached to the handle; and a surgical implant removably attached to the distal end of the shaft, wherein the at least one suture is threaded through the surgical implant.

31. The apparatus of claim 30 wherein the handle comprises a movable portion, wherein the movable portion has at least a first position and a second position, wherein the movable portion contacts the spool in at least the second position thereby preventing the rotation of the spool with respect to the handle in the direction that would allow the at least one suture to unwind.

32. The apparatus of claim 31 wherein the handle comprises an inner chamber, and wherein the spool is located in the inner chamber of the handle.

33. The apparatus of claim 31 comprising two sutures, each comprising a first end and a second end that are wound around the spool, wherein the two sutures are each threaded through the surgical implant.

34. The apparatus of claim 30 wherein the handle comprises an inner chamber, and wherein the spool is located in the inner chamber of the handle.

35. The apparatus of claim 30, wherein the device is a suture anchor.

36. The apparatus of claim 30 or 31 wherein the spool comprises one or more slots, wherein at least one suture comprises one or more needles, and at least one needle is located in a slot on the spool.

37. The apparatus of claim 30 wherein the distal end of the shaft comprises a recess, wherein at least the proximal end of the surgical implant is located in the recess.

38. A method of using the apparatus of claim 30, 31, or 34, comprising:
inserting the distal end of the shaft into body tissue;
attaching the surgical implant to a portion of the body tissue;
unwinding the at least one suture from the spool; and
securing body tissue to the surgical implant by tying the at least one suture.

39. An apparatus for inserting surgical implants in vivo, comprising:
a handle, comprising a door portion that may be positioned in at least an open and a closed position,
a spool rotatably attached to the handle;
at least one suture having a first end and a second end, wherein each end of the at least one suture is wound around the spool;
a shaft having distal and proximal ends, wherein the proximal end is attached to the handle; and
a surgical implant removably attached to the distal end of the shaft, wherein the at least one suture is threaded through the surgical implant, wherein when the door is in the closed position, the contact between the door portion and the spool prevents the spool from rotating with respect to the handle in the direction that would allow the at least one suture to unwind;
and wherein, when the door portion is in the open position, the door portion does not prevent the spool from rotating with respect to the handle in the direction that would allow the at least one suture to unwind.

40. The apparatus of claim 39 wherein the door portion comprises a protrusion that contacts the spool at least when the door portion is in the closed position.

41. The apparatus of claim 40 wherein the spool comprises at least one notch aligned to receive the protrusion on the door portion at least when the door portion is in the closed position.

42. The apparatus of claim 41 wherein the spool comprises a series of notches encircling the circumference of the spool aligned such that at least one of the notches receives the protrusion on the door portion at least when the door is in the closed position.

43. The apparatus of claim 39 wherein the door portion moves from the closed position to the open position by pivoting.

44. The apparatus of claim 39 wherein the door portion moves from the closed position to the open position by sliding.

45. The apparatus of claim 39 wherein the door portion moves from the closed position to the open position by rotating.

46. The apparatus of claim 39 further comprising a first and a second suture, each comprising a first end and a second end that are wound around the spool, wherein
the first and the second sutures are threaded through the surgical implant.

47. The apparatus of claim 46 wherein the distal end of the shaft comprises a recess, wherein at least the proximal end of the surgical implant is located in the recess.

48. The apparatus of claim 47 wherein the distal end of the shaft further comprises a longitudinal slot extending from the distal tip of the shaft towards the proximal end of the shaft, wherein the first and second sutures pass through the longitudinal slot on the distal end of the shaft.

49. The apparatus of claim 48 wherein the first suture comprises a first needle attached to its first end, and a second needle attached to its second end, and the second suture comprises a third needle attached to its first end, and a fourth needle attached to its second end.

50. The apparatus of claim 49 wherein the spool comprises a first, second, third, and fourth slots, and wherein the first needle is located in the first slot, the second needle is located in the second slot, the third needle is located in the third slot, and the fourth needle is located in the fourth slot.

51. The apparatus of claim 39 wherein the spool comprises at least two grooves, and wherein each end of each suture is located in a separate groove on the spool.

52. An apparatus of for inserting surgical implants in vivo, comprising:
a handle;
a spool rotatably attached to the handle, the spool comprising four slots;
two sutures, each comprising a first end and a second end that are wound around the spool, each end of the two sutures comprising a needle, each needle located in one of the four slots;
a shaft having distal and proximal ends, wherein the proximal end is attached to the handle; and
a surgical implant removably attached to the distal end of the shall, wherein the two sutures are each threaded through the surgical implant.

53. An apparatus for inserting surgical implants in vivo, comprising:
a handle;
a spool rotatably attached to the handle;
at least one suture having a first end and a second end, wherein each end of the at least one suture is wound around the spool;
a shaft having distal and proximal ends, wherein the proximal end is attached to the handle and the distal end comprises a longitudinal slot extending from a distal tip of the shaft towards the proximal end of the shaft, wherein the at least one suture passes through the longitudinal slot on the distal end of the shaft; and a surgical implant removably attached to the distal end of the shaft, wherein the at least one suture is threaded through the surgical implant.

54. The apparatus of claim 53 comprising a first and a second suture, each comprising a first end and a second end that are wound around the spool, wherein the first and the second sutures are threaded through the surgical implant and pass through the longitudinal slot on the distal end of the shaft.

55. The apparatus of claim 54 wherein the first suture comprises a first needle attached to its first end, and a second needle attached to its second end, and the second suture comprises a third needle attached to its first end, and a fourth needle attached to its second end.

* * * * *